United States Patent [19]

Levine

[11] 4,051,848
[45] Oct. 4, 1977

[54] SYNTHETIC SKIN WOUND DRESSING

[76] Inventor: Norman S. Levine, 237 Arlingham Road, Flourtown, Pa. 19031

[21] Appl. No.: 662,748

[22] Filed: Mar. 1, 1976

[51] Int. Cl.$^2$ .............................................. A61L 15/00
[52] U.S. Cl. ..................................................... 128/156
[58] Field of Search .................... 128/155, 156, 296; 428/190, 224, 246, 284, 298, 315

[56] References Cited

U.S. PATENT DOCUMENTS

| 2,682,873 | 7/1954 | Evan et al. | 128/156 |
| 3,526,224 | 9/1970 | Potts | 128/156 |
| 3,545,442 | 12/1970 | Wicker et al. | 128/296 |
| 3,824,996 | 7/1974 | Carlisle | 128/156 |
| 3,949,742 | 4/1976 | Nowakowski | 128/155 |
| 3,971,381 | 7/1976 | Gibson | 128/296 |
| 3,972,328 | 8/1976 | Chen | 128/156 |

Primary Examiner—John D. Yasko
Attorney, Agent, or Firm—Seidel, Gonda & Goldhammer

[57] ABSTRACT

A wound dressing which acts as a temporary synthetic skin is provided for the eventual healing of tissue partially or completely denuded of skin. The dressing is a unitary structure which is stretchable in two dimensions and is comprised of an outer component and an inner component. The outer component is a microporous membrane permeable to gases but impermeable to micro-organisms. The inner component is a three dimensional matrix structure made of at least two substantially coextensive layers of knitted fabric each bound into the other at closely spaced points to retain stretchability. Each fabric layer is knitted from threads spaced from each other at such a distance that cellular elements from the denuded tissue may invade the dressing to promote healing. The inner component must be thick enough to allow for uniform invasion by cellular elements from the denuded wound, but not so thick so as to allow a large portion of the dressing to be filled by tissue exudates and body fluids, rather than cellular elements representing fibroblastic ingrowth, and not so thick as to prevent infection within such an accumulation from being recognized.

12 Claims, 5 Drawing Figures

SYNTHETIC SKIN WOUND DRESSING

STATEMENT OF GOVERNMENT INTEREST

Applicant has granted to the Government Of The United States of America as represented by the Secretary Of The Army a non-exclusive, irrevocable, royalty-free license throughout the world in the invention of this application and under any patent domestic or foreign which is or may be granted thereon, with power to grant licenses for all governmental purposes.

BACKGROUND OF THE INVENTION

This invention relates generally to a surgical-medical dressing designed to conform and adhere to areas of tissue either completely or partially denuded skin, and acts as a temporary synthetic skin. The wound is protected from exterior microbial attack and allows cellular elements of the tissue to become embedded with the dressing.

This synthetic skin is used primarily to cover tissue denuded of skin. The term "tissue denuded of skin" refers to any tissue which partially or completely has lost its skin coverage. Such tissue can represent fat, muscle, fascia, bone, tendon, cartilage, blood vessel, nerve or granulation tissue.

Such tissue denuded of skin can be clean, wherein no debris covers the exposed tissue. It can also be incompletely clean, wherein particles of debris (non-viable tissue, wound exudate, dried blood, etc.) are scattered throughout the wound. Tissue denuded of skin is found in a variety of illnesses, including skin abrasions, surgical wounds and amputations wherein the skin is not closed, decubitus ulcers, and burns, after the thermally injured skin has partially or completely separated from the underlying tissue. In certain deep burns, the skin has completely been destroyed and the physician may choose to treat the burn by removing all of the destroyed skin, leaving an exposed area of tissue denuded of skin.

Tissue denuded of skin presents several problems because of the loss of skin, among them: a barrier against external infection is lost, vital body fluids (water, electrolytes and protein) are lost through the open surface, and infection occurs in tissue denuded of skin because of proliferation of micro-organisms in the wound debris. In burns, microbial proliferation occurs in the thermally injured tissue, and in other wounds microbial proliferation occurs in the coagulum of blood and tissue fluids which accumulate in the wound surface.

Basic principles of therapy require that wound debris be removed from the wound surface. This includes necrotic tissue, wound exudate, foreign particles, dried blood, etc. A barrier against infection from the environment external to the wound must be provided. The infection already present in the wound must be controlled and the loss of vital body fluids from the wound must be reduced. Finally, the restoration of skin function is provided for by surgical replacement of the patient's own skin.

If the tissue is completely clean, it may be covered with the patient's own skin by means of a full-thickness or a partial-thickness skin graft or by means of a skin flap. Several situations arise in which the use of the patient's own skin is inadvisable. First, the denuded surface may be incompletely clean, in which case a skin graft may not be successful. Second, on an area of clean tissue partially denuded of skin, it would be desirable to apply a skin-like dressing; however, because such an area will heal without grafting, in time, it is not justifiable to use the patient's own skin as a temporary cover. Third, the patient may be too sick to tolerate an anesthetic and surgical procedure required to harvest skin grafts from him. Fourth, as in the case of massive third-degree burns, there may be insufficient amounts of the patient's own skin to cover the larger area denuded. In such cases, substitutes for the patient's own skin have been used advantageously.

DESCRIPTION OF THE PRIOR ART

Temporary substitutes for the patient's own skin have included skin harvested from human cadavers (allograft), skin from animals of other species (xenograft) and human amnionic membranes. These materials are known as "biologic dressings" and are used to temporarily achieve the functions of skin.

For denuded wounds which are incompletely clean, other forms of treatment have been used. A variety of creams, ointments, and synthetic films have been used to cover the area denuded of skin without adhering to the wound. Topically applied antimicrobial agents have been used to lower the number of micro-organisms populating the wound surface. Other materials have been used which adhere to the burn surface, such as nylon velour, polyvinyl alcohol sponge, and gauze wrappings. Such dressings, when changed frequently, can effectively debride (remove dead tissue from) the wound surface. Micro-organisms may profilterate in the debris and wound exudate which accumulate in these dressings.

Recently, a few dressings have been proposed to serve as synthetic skin substitutes for use in treating wounds denuded of skin. One such dressing, produced by Edwards Laboratories, consists of a single layer of woven, coarse mesh cotten gauze adhered to a silicone rubber membrane. The gauze is designed to serve as a "scaffolding layer" to adhere to the denuded tissue, and the silicone rubber surface is designed to protect the wound from infection from the environment and to reduce protein, fluid, and electrolyte losses from the wound. Although such a dressing adheres to the wound initially, the dressing is not invaded by cellular elements from the wound and fluid accumulates in the form of blisters and pockets of wound exudate under the dressing.

Another dressing, Epigard, is described in U.S. Pat. No. 3,648,692 issued to Parke-Davis Company. An open cell foam or sponge made of polyurethane is used to adhere to the wound, the foam in turn is adhered to a gas permeable membrane which is impermeable to fluids and bacteria. This dressing adheres well to wounds and serves as an effective debriding agent. This dressing has the disadvantages of being somewhat stiff and therefore difficult to drape over irregular wound contours, and is also so thick that microbial growth is allowed within the dressing. Thus, because of its sponge-like construction, the dressing tends to accumulate pus, which may be obscured when one views the external surface of the dressing.

Another dressing is disclosed in U.S. Pat. No. 3,903,882, issued to American Cyanamide Company. This dressing consists of a vapor permeable elastomeric film as the outer component which is bonded to a knitted fabric of tissue absorbable polymer, such as polyglycolic acid, as the inner component. The use of polyglycolic acid is of questionable advantage because, in practice, the dressing would be changed before the tissue absorbable material is absorbed by the body. The single layer of tricot knit fabric is not optimal for obtaining fibroblastic ingrowth and thus may allow the undesirable formation of a scab underneath the dressing.

U.S. Pat. No. 3,526,224, issued to Johnson & Johnson, discloses a dressing having an elastomeric polyurethane film as the outer component bonded to a sheet of velour fabric. A serious disadvantage of this dressing is that it allows fragmentation of the velour loops into the wound. This may increase the chances of environmental infection, rather than decreasing these chances.

U.S. Pat. No. 3,824,996, issued to Richard Carlisle, describes a non-woven, non-elastic material designed to minimize stretch and to allow inter-layer sliding. The dressing of the present invention is designed to eliminate such inter-layer sliding and to maximize stretch and is a unitary structure. The Carlisle patent indicates that some layers of the dressing may be left on the wound while others may be peeled off. This factor is contrary to the teaching of the present invention.

U.S. Pat. No. 3,867,935, issued to Johnson & Johnson, teaches a dressing comprising a plurality of plys of a non-woven textile-like material of mechanically entangled fibers. This patent emphasizes its high capacity for absorption of body fluids. Absorption is not a desired property in the wound dressing of the present invention. Although some absorption of body fluids into the present invention must occur to precede fibroblastic ingrowth, too much absorption is in fact undesirable, because it provides a good milieu for bacterial proliferation underneath the outer component.

SUMMARY OF THE INVENTION

To obviate the above-described disadvantages, a unitary three-dimensional matrix adhered to a microporous membrane is provided as a temporary synthetic skin. The dressing conforms easily to irregular wound surfaces and adheres well, as well as preventing micro-organisms in the environment from contaminating the wound surface. The dressing is designed for penetration by cellular elements from the wound surface, creating fibroblastic ingrowth which permits phagocytic cellular elements to ingest and kill microbial wound contaminants within the dressing. The loss of vital body fluids from the denuded tissue is limited without permitting fluid collection between the denuded tissue and the dressing. The dressing may be used as a temporary skin substitute for clean wounds denuded of skin or to debride incompletely clean tissue denuded of skin.

The dressing having these advantages is made of at least two layers, and preferably four or more layers, of knitted fabric having a thickness and thread spacing suitable for uniform invasion by cellular elements from the denuded tissue. Each knitted fabric layer is bonded to the other at closely spaced points which still allow the dressing to be stretchable in two dimensions. A microporous, gas permeable, micro-organism impermeable membrane may be bonded to the knitted fabric layers in any suitable manner, consistent with maximum stretching, for the purpose of preventing environmental contamination of the wound.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

Figure 1:
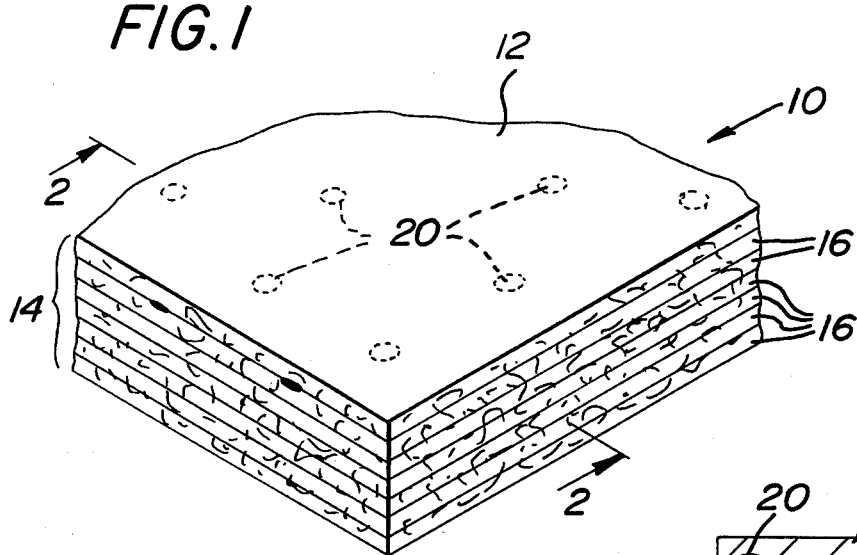
FIG. 1 is a perspective view of the synthetic skin wound dressing in accordance with the present invention.

Referring to the drawings in detail, wherein like numerals indicate like elements throughout the several views, there is shown in FIG. 1 a synthetic skin wound dressing in accordance with the present invention designated generally as 10. Dressing 10 consists of an outer component 12 and an inner component 14, which is a unitary three-dimensional matrix structure.

Outer component 12 is a thin, microporous membrane, which is permeable to gases and impermeable to micro-organisms. It may or may not be permeable to liquids, as desired. This membrane should be as thin as is compatible with a reasonable structurally integrity so that it will not fall apart with routine handling. Preferably, it should be approximately 0.5 to 10 mils in thickness and should be stretchable in two dimensions. The pore size may vary from about 0.01 to about 1 micron in diameter. It may be manufactured from any one of a number of materials, such as, for example, polytetrafluoroethylene film (such as available from Gore & Associates, Newark, DE.), vulcanized latex, silicone rubber, or polypropylene films (Celanese Corp.).

Figure 2:
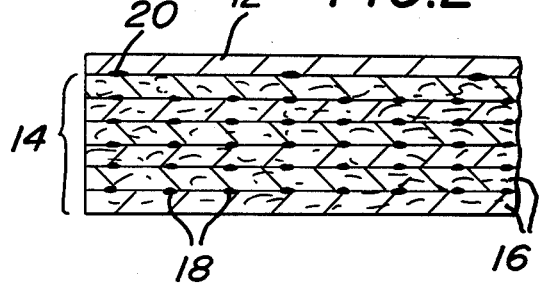
FIG. 2 is a sectional view of the dressing taken along line 2—2 of FIG. 1, showing the bonding of the knitted fabric layers and the microporous membrane.

Inner component 14 is comprised of at least two layers 16, and preferably about 4 to 8 layers, of stretchable knitted fabric. As best shown in FIG. 2, the individual knitted layers 16 are bonded to each other at spaced points 18 which allow the multilayered structure to remain very conformable and stretchable in two dimensions.

The manner in which each individual layer of fabric is knitted is important. The threads from which each layer is knitted should be spaced from each other at a distance of about 5 microns to 5 millimeters (5000 microns), and preferably about 50 to 2000 microns. This represents a large enough void size within each layer of knitted fabric to permit fibroblastic ingrowth. If the void size, defined by the thread spacing, is much larger than 5 millimeters, the dressing will not be anchored securely to the underlying tissue. If the void size is less than about 5 microns in diameter, a typical dimension for a fibroblast, then fibroblastic cellular ingrowth will be prevented.

The degree of fibroblastic cellular ingrowth is also dependent to a large degree on the thickness of inner component 14. The thickness, or loft, of the inner component will be determined by the number of knitted layers 16 used to make up inner component 14, the loft of each knitted layer 16, and the denier of each individual thread used to knit the layers 16. The overall thickness of the inner component 14 should be from about 10 to 200 mils. The minimum acceptable thickness is that which permits invasion of the inner component of the dressing by cellular elements from the tissue denuded of skin. Before invasion of this dressing by cellular elements from the wound can occur, a certain amount of absorption of body fluids and exudates from the wound by the dressing must occur. If the inner component of this dressing is too thick, a large portion of the dressing will be filled by tissue exudates and body fluids and not by cellular elements from the wound, and these fluids and exudates may be hidden within the dressing. Such a situation is undesirable because body fluids and wound exudates form a good environment for the proliferation of micro-organisms unless cellular tissue elements are present to decontaminate the area by phagocytosis and other means. The presently preferred embodiment of the inner component 14 is one having a thickness from about 16 to 32 mils made from between 4 and 8 layers of knitted fabric.

The threads from which the fabric is knitted may be of any fine denier natural or synthetic fiber material such as, for example, polyamides, rayon, dacron, polyester, cotton, silk, cat gut, polyglycolic acid, Prolene (a trademark of Ethicon Corp. for a polypropylene synthetic textile fiber), Mersilene (a trademark of Ethicon Corp), Tevdek (a trademark of Deknatel Corp.). Certain thread-like materials, e.g., cat gut, cotton, and silk, when placed in contact with a wound denuded of skin will evoke more of an inflammatory response from the tissue than others, e.g., nylon, Prolene, Mersilene. In general, materials which include less of an inflammatory response are preferred. Fabrics having non-fragmenting fibers or threads are preferred, preferably continuous filament rather than staple fibers. The threads may be single or multi-filament threads and may or may not be treated with a coating material.

The denier of the threads should be as fine as it compatible with reasonable structural integrity of the knit layers, preferably from about 5–50 denier. As used herein, the term "knitting" will be understood to include weaving or other similar forms of thread engagement. Any technique of knitting is acceptable, provided that it allows the individual knit layers 16 to be very conformable and somewhat stretchable in two dimensions. Micromesh stocking knit, for example that knitted from 15 denier nylon 66, using a 3 × 1 mesh stitch micromesh knit, and stretch support stocking knits are examples of acceptable knits.

The individual knitted layers 16 are bonded to each other by any suitable bonding methods compatible with stretchability and conformability. For example, ultrasonic bonding or thermal fusion of the threads of the knitted layers at closely spaced, interrupted points is suitable, as depicted by bonding areas 18 in FIG. 2. Although the bonds 18 in FIG. 2 are shown, for ease of illustration as point bonds between adjacent layers, it will be understood that the spaced bonds may extend entirely or substantially through the layers 16 of the inner component 14, as would usually be the case with ultrasonic bonding or thermal fusion. Further, for ease of illustration, layers 16 have been shown out of proportion in thickness and without deformation at the bonding points, whereas in actuality compressions of the layers are formed by ultrasonic or thermal fusion.

Figure 3:
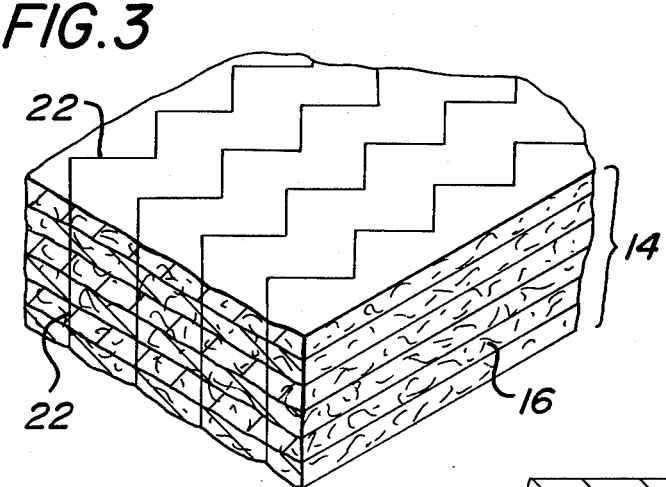
FIG. 3 is a sectional view of a dressing similar to that of FIG. 2, showing an alternate method of bonding the knitted fabric layers, but without a microporous membrane.
Figure 5:
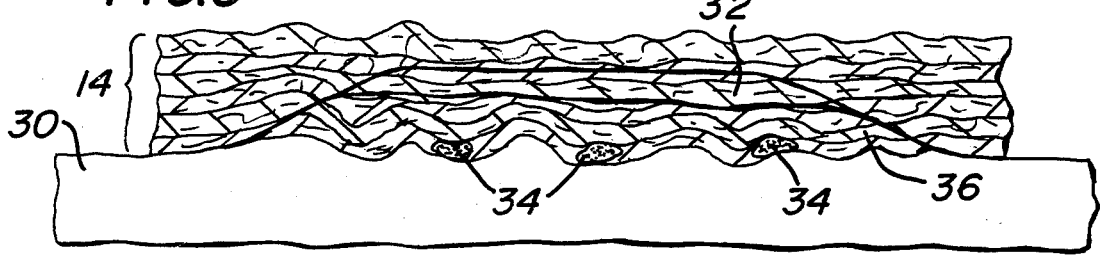
FIG. 5 is an enlarged, partial sectional view similar to that of FIG. 4, showing the application of the invention to an incompletely clean tissue denuded of skin, wherein the microporous membrane is absent.

Another method of bonding the individual layers 16 together is to use several separated zig-zag stitches 22 through all knit layers to hold them together. This is depicted in FIG. 3, which shows a unitary synthetic skin wound dressing composed solely of a plurality of knitted fabric layers 16. The use of this embodiment alone, without the outer component, is shown in FIG. 5, to be described below. Another method of binding individual layers 16 together is to use interrupted, tied threads (not shown) placed in such a fashion that they secure the several layers together. Still another method would be to knit one layer of knitted fabric 16 to the immediately adjacent layer, which in turn is knitted to the next adjacent layer.

The spacing between the various bonds uniting individual knitted fabrics layers 16 is important, not only in allowing the maximum stretchability and conformability, but also in creating a unitary structure. Inner component 14 serves as a scaffolding layer to adhere to the denuded tissue and which the cellular elements of the wound can invade. If the bonding points are spaced too far apart, the structural integrity of the matrix would be compromised and separation of adjacent knit layers might occur and could allow an entire knit layer to be retained by the wound. If the bonding points are too close together, the stretch of the dressing can be compromised. Thus, bonding points, advantageously spaced from each other at intervals from about 0.01 to 0.5 inch, and preferably about 0.1 to 0.25 inch, will allow for integrity and adequate spacing of the matrix without compromising stretch. If layers 16 are knitted together rather than bonded, closer spacing of the connecting points could be used without compromising stretch.

As best shown in FIG. 2, outer component 12 is bonded to inner component 14, where it is desired to protect the wound from environmental contamination. The bond between the outer and inner components should not impair the desired membrane characteristics of outer component 12 and should allow conformability and two dimensional stretch of the entire dressing 10. It is desirable to use a bonding system containing numerous separated points or lines of adhesion rather than a continuous layer of an adhesive substance. Such interrupted points are represented as bonding points 20 as best shown in FIGS. 1 and 2. An example of a suitable bonding technique would be a dot-adhesive pattern, such as a diamond dot-adhesive pattern, using a polyethylene powder to heat-seal inner component 14 to outer component 12. Another acceptable adhesive pattern is the use of Delnet adhesive. Alternatively, the same bonding method may be used to bond outer component 12 to inner component 14 as was used to bond individual knitted fabric layers 16 to each other. Another technique would be to place two or more layers of knitted fabric 16 on the other side of outer component 12 and to bond all of the knitted layers of material together in one operation with the bonds extending through component 12.

The spacing between the bond points 20 bonding outer component 12 to inner component 14 may be the same, smaller, or greater than the spacing between bonding points 18 which bond inner component knitted fabric layers 16 to each other.

Outer component 12 may be translucent. This would allow ready recognition of blood or infection under or within the dressing, should such an accumulation occur. Healing may thus be more readily monitored.

Figure 4:
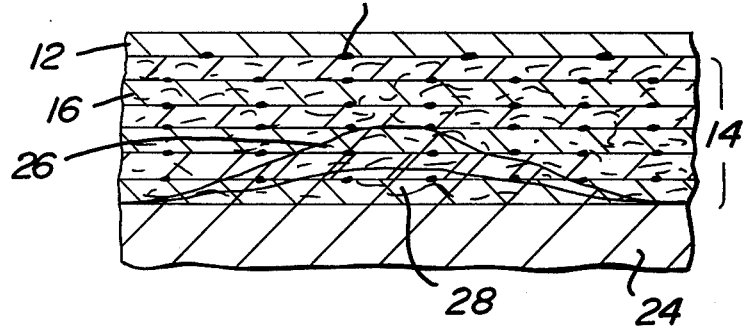
FIG. 4 is an enlarged, partial sectional view similar to that of FIG. 2 representing the application of the invention to a completely clean tissue denoded of skin.

FIG. 4 represents the application of the synthetic skin wound dressing comprising inner component 14 and outer component 12 to a completely clean tissue denuded of skin. In general, the dressing should be used as a short-term synthetic skin and should be changed more frequently than every four to five days. Under special circumstances, it may be used as a long-term dressing and may be left in place for more than five days. It may be used with or without solutions containing antimicrobial agents, such as, for example, a solution containing 5% mafenide acetate (Sterling-Winthrop Corp.) in sterile water. The antimicrobial solution will be absorbed by the mesh knit and seems to aid in controlling microbial growth on the tissue denuded of skin. Any of a variety of chemotherapeutic and antimicrobial solutions may be used.

Turning now to FIG. 4, dressing 10 is placed on tissue 24, completely clean and denuded of skin, with the inner component adjacent to the wound. Within minutes after application of the dressing, vital body fluids and wound exudates 26 will begin to accumulate within the inner component of the dressing. These body fluids and tissue exudates contain several clotting elements which will temporarily bind inner component 14 to the surface of the wound. The accumulation of these body fluids and tissue exudates also provides a suitable environment in which the cellular elements from the denuded tissue may invade the inner component of the dressing. Such tissue elements will contain phagocytes which may ingest and kill micro-organisms and also fibroblasts which will deposit collagen and other tissue elements to reinforce the bond between the tissue surface and the inner component of the dressing. The highly conformable and stretchable nature of the dressing allows it to contour to irregular surfaces of the wound.

Outer component 12 functions as a barrier to prevent infection in the environment from reaching the tissue surface. Because the outer component is gas permeable, it allows air to reach the wound surface and hence does not permit anaerobic conditions in the wound which would be a particularly suitable environment for the growth of *Cl. Perfringens* and other anaerobic pathogens. By virtue of gas permeability, it permits the evaporation of water from the wound and does not allow the accumulation of water under pressure under the dressing. This avoids problems of blister formation and pockets and other body fluids and wound exudates from forming under the dressing.

Although outer component 12 should be permeable to gases, it may or may not be permeable to liquids. For most purposes, water impermeability is not necessary as the aforementioned clot, which is formed by the body fluids and tissue exudates within the inner component, will, to a large degree, control the losses of vital body fluids.

When the dressing is removed from the tissue denuded of skin, a clean wound bed should again be present, which may then be covered with the patient's own skin, biologic dressing or a reapplication of the dressing 10. Numeral 28 in FIG. 4 represents the invasion of cellular tissue elements, fibroblasts and phagocytes, from the wound to the dressing. When the dressing is removed from the wound, this layer of cellular tissue elements 28 and wound exudates 26 will be removed, leaving clean tissue 24 for the application of different dressings or the reapplication of the dressing of the present invention.

Examples of this particular application are deep skin abrasions, exposed tissue following amputations or other surgical wounds in which the skin was not closed, decubitus ulcerations (bed sores) after they have been cleaned of debris, full thickness burns, from which the dead tissue has been debrided, clean fascial surfaces after surgical excision of burn wounds, or any other area of skin loss.

FIG. 5 is a schematic representation of the application of this invention, absent the other component, to areas of tissue denuded of skin which are incompletely clean. Such wounds contain wound debris 34 is some areas, but other areas are completely clean. The principle of care for wounds is to remove the debris to obtain a clean wound surface. Such wounds may be debrided by application of the dressing with the inner component placed in contact with the wound. The dressing will absorb body fluids and tissue exudates 32 as it does for clean tissue denuded of skin. Clot formation within the inner component allows adherence of the dressing to the wound and is followed by invasion of the dressing by cellular tissue element 36 from the clean areas of the wound. Because of this adherance, removal of the dressing is accompanied by debridement of areas of wound debris.

Examples of such incompletely clean tissue denuded of skin are abrasions containing particulate matter, decubitus ulcers, and full-thickness burns from which the thermally injured tissue has not completely separated from the underlying tissue. Because of the micro-organism and infection-causing agents present in the areas of debris 34, the protection from environmental contamination, provided by outer component 12, may not be necessary. In treating such wounds, therefore, either the inner component alone or the full dressing may be used.

Tissue which has been incompletely denuded of skin occurs in a variety of situations including skin abrasions which do not extend through the full thickness of skin; partial thickness burns, wherein only the outermost layers of skin are destroyed, after the thermally injured tissue has in part been removed from the underlying tissue; and donor sites from which a partial thickness skin graft has been surgically removed. In these wounds, the epidermis has been lost. Such wounds will heal without the need for skin grafting. These wounds heal by virtue of the coalescence of small areas of dermal eithelium located in the deep thermal elements, such as the hair shafts, which extend below the epidermal layer of skin.

The use of the invention for these injuries is designated as a temporary wound cover to protect the areas of the wound which are not covered by epithelium while the dermal epithelial elements coalesce underneath the dressing.

In certain situations, it may be desirable to leave the dressing on the wound for periods of five days or longer. Examples of such situations would be in patients with extensive burns when not enough skin can be harvested from the patient himself to cover all of the clean tissue which is denuded of skin, or in the case of a patient treated by large scale surgical excision, who represents a large area of tissue denuded of skin, for which it might be desirable to use a long-term substitute for the patient's own skin. In these and other situations, the dressing works by the mechanisms described for clean tissue denuted of skin. Because of the maturation of the cellular ingrowth into the dressing, however, it becomes difficult, after the dressing has been in place for move than five days, to simply strip the dressing from the underlying tissue. If the dressing has been kept on the wound for more than five days, it may be necessary to surgically remove it from the underlying tissue.

The present invention may be embodied in other specific forms without departing from the spirit or essential attributes thereof and, accordingly, reference should be made to the appended claims, rather than to the foregoing specification as indicating the scope of the invention.

I claim:

1. A unitary wound dressing comprising an inner component for application to tissue denuded of skin, and an outer component bonded to and substantially coextensive with said inner component, said inner component being made of at least two substantially coextensive layers of knitted fabric each bonded to the other at closely spaced points which will allow said inner component to readily stretch in two dimensions, said inner component having a thickness and thread spacing suitable for uniform invasion by cellular elements from said denuded tissue, said outer component comprising a stretchable membrane which is permeable to gases, but impermeable to microorganisms.

2. A dressing as defined in claim 1 wherein said inner component has a thickness of from about 10-200 mils, each of said knitted fabric layers being knitted from threads of from about 5-50 denier, such that the spacing between the threads of a knit layer is from about 5 microns to 5 millimeters, said knitted fabric layers bonded to each other at points spaced from each other from about 0.01-0.50 inch, said outer component being a microporous membrane having a pore size which may vary from about 0.01 to 1 micron in diameter, and said outer component having a thickness of from about 0.5 to 10 mils.

3. A dressing as defined in claim 1 wherein said outer component is a microporous membrane made of materials selected from the group consisting of polytetrafluoroethylene, silicone rubber, vulcanized latex and polypropylene and said inner component is made from several layers of fabric knited from threads which are selected from the group consisting of polyamides, polyesters, polyesters, polyglycolic acid, cotton, silk, cat gut, dacron, polypropylene and rayon.

4. A wound dressing as defined in claim 1 wherein said inner component has a thickness from about 16 to 32 mils and is made from between 4 and 8 layers of fabric knitted from 15 denier nylon 66 using a 3 × 1 mesh stitch micromesh weave, said layers being bonded together by point bonds separated from each other by about 0.125 inch in a diamond bond pattern, said inner component being bonded to said outer component by any means which allows substantial two dimensional stretchability.

5. A wound dressing as defined in claim 1 wherein said outer component is translucent.

6. A wound dressing as defined in claim 1 wherein said dressing is impregnated with an antimicrobial agent.

7. A wound dressing as defined in claim 1 wherein said outer component is liquid impermeable.

8. A three-dimensional unitary surgical-medical dressing comprising at least two substantially coextensive layers of knitted fabric, each layer bonded to the other to closely spaced points which allow said dressing to stretch in two dimensions, said layers being of a sufficient number to produce a dressing having a thickness suitable for fibroblastic ingrowth to anchor said dressing to tissue denuded of skin, but not so thick as to allow a large portion of the dressing to become filled by tissue exudates and body fluids, said fabric layers being knitted from thread such that said threads of each layer are spaced far enough apart to permit invasion by cellular tissue elements but close enough to allow for secure adherence of said dressing to the tissue.

9. A dressing as defined in claim 8 wherein said fabric layers are knitted from non-fragmenting threads selected from the group consisting of polyamides, polyesters, polyglycolic acid, cotton, silk, cat gut, dacron, polypropylene and rayon.

10. A dressing as defined in claim 8 wherein said dressing has a thickness of from about 10-200 mils, each of said knitted fabric layers being knitted from threads of from about 5-50 denier, such that the spacing between the threads of a knit layer is from about 5 microns to 5 millimeters, and said knitted fabric layers bonded to each other at points spaced from each other from about 0.01-0.50 inch.

11. A dressing as defined in claim 8 wherein said dressing has a thickness from about 16 to 32 mils and is made from between 4 and 8 layers of fabric knitted from 15 denier nylon 66 using a 3 × 1 mesh stitch micromesh weave, and said layers being bonded together by point bonds separated from each other by about 0.125 inch in a diamond bond pattern.

12. A dressing as defined in claim 8 wherein said dressing is impregnated with an antimicrobial agent.

* * * * *